US006723303B1

(12) United States Patent
Quay

(10) Patent No.: US 6,723,303 B1
(45) Date of Patent: *Apr. 20, 2004

(54) ULTRASOUND CONTRAST AGENTS INCLUDING PROTEIN STABILIZED MICROSPHERES OF PERFLUOROPROPANE, PERFLUOROBUTANE OR PERFLUOROPENTANE

(75) Inventor: Steven C Quay, Pacific Palisades, CA (US)

(73) Assignee: Amersham Health, AS, Oslo (NO)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1,675 days.

(21) Appl. No.: 08/466,104

(22) Filed: Jun. 6, 1995

Related U.S. Application Data

(63) Continuation of application No. 08/380,085, filed on Jan. 30, 1995, now Pat. No. 5,558,854, which is a division of application No. 07/936,011, filed on Sep. 2, 1992, now abandoned, which is a continuation-in-part of application No. 07/893,657, filed on Jun. 5, 1992, now Pat. No. 5,409,688, which is a continuation-in-part of application No. 07/761,311, filed on Sep. 17, 1991, now abandoned.

(51) Int. Cl.$^7$ ................................. A61B 8/00
(52) U.S. Cl. ..................................... 424/9.52
(58) Field of Search .................. 424/9.5, 952, 673; 128/662.02, 661.02, 660.01; 514/744, 746, 752, 754, 757

(56) References Cited

U.S. PATENT DOCUMENTS

| | | |
|---|---|---|
| 4,265,251 A | 5/1981 | Tickner |
| 4,276,885 A | 7/1981 | Tickner et al. |
| 4,442,843 A | 4/1984 | Rasor et al. |
| 4,466,442 A | 8/1984 | Hilmann et al. |
| 4,533,254 A | 8/1985 | Cook et al. |
| 4,544,545 A | 10/1985 | Ryan et al. |
| 4,572,203 A | 2/1986 | Feinstein |
| 4,657,756 A | 4/1987 | Rasor et al. |
| 4,681,119 A | 7/1987 | Rasor et al. |
| 4,684,479 A | 8/1987 | D'Arrigo |
| 4,718,433 A | 1/1988 | Feinstein |
| 4,767,610 A | 8/1988 | Long |
| 4,774,958 A | 10/1988 | Feinstein |
| 4,832,941 A | 5/1989 | Berwing et al. |
| 4,844,882 A | 7/1989 | Widder et al. |
| 4,859,363 A | 8/1989 | Davis et al. |
| 4,865,836 A | 9/1989 | Long, Jr. |
| 4,895,876 A | 1/1990 | Schweighardt et al. |
| 4,900,540 A | 2/1990 | Ryan et al. |
| 4,927,623 A | 5/1990 | Long, Jr. |

(List continued on next page.)

FOREIGN PATENT DOCUMENTS

| | | |
|---|---|---|
| AU | 8930351 | 8/1989 |
| AU | 9170982 | 10/1991 |
| CN | 87105799 | 4/1988 |
| DE | 4100470 | 3/1925 |
| DE | 3834705 A1 | 4/1990 |
| DE | 4127442 A1 | 2/1993 |
| EP | 0077752 A2 | 4/1983 |
| EP | 0231091 A1 | 8/1987 |
| EP | 0245019 A2 | 11/1987 |
| EP | 0307087 A1 | 3/1989 |
| EP | 0324938 A1 | 7/1989 |
| EP | 0327490 A1 | 8/1989 |
| EP | 0357163 A1 | 3/1990 |
| EP | 0359246 A2 | 3/1990 |
| EP | 0454044 A2 | 10/1991 |
| EP | 0458745 A1 | 11/1991 |
| EP | 0467031 A2 | 1/1992 |
| EP | 0494615 A1 | 7/1992 |
| EP | 0502814 A2 | 9/1992 |
| EP | 0554213 A1 | 8/1993 |

(List continued on next page.)

OTHER PUBLICATIONS

American Heart Assoication, Abstracts of the 58th Scientific Sessions, Circulation 72: Oct. 1985 III–427.
Association of University Radiologists Association of University Radiologists Proceedings of Annual Meeting, Journal of Clinical and Laboratory Research Investigative Radiology 17:4, Abstract 110 (1982).
Bleeker, H., et al., On the Application of Ultrasonic Contrast Agents for Blood Flowmetry and Assessment of Cardiac Perfusion, Journal of Ultrasound in Medicine, 9:461–471 (1990).
Bleeker, H., et al., Ultrasonic Characterization of Albunex, and New Contrast Agent, Journal Accoustical Society of America. 87:1792–1797 (1990).
Bommer, W.J., et al., Report of the American Society of Echocardiography: Contrast Echocardiography, Jun. 1984.
Davis, P.L., et al., Echogenicity Cause by Stable Microbubbles in a Protein–Lipid Emulsion, The Journal of Clinical Ultrasound. 9:249–252, Jun. 1981.
De Jong, N., et al., Absorption and Scatter of Encapsulated Gas Filled Microspheres: Theoretical Considerations and Some Measurements, Ultrasonics, 30:95–103 (1992).
De Jong, N., et al., Principles and Recent Developments in Ultrasound Contrast Agents, Ultrasoncis 29:324–330, Jul. 1991.
Epstein, P.S., et al., On the Stability of Gas Bubbles in Liquid–Gas Solutions, Journal of Chemical Physics 18:1505–1509, Nov., 1950.

(List continued on next page.)

Primary Examiner—Michael G. Hartley
(74) Attorney, Agent, or Firm—Townsend and Townsend and Crew, LLP

(57) ABSTRACT

Agents for use in ultrasound contrast include protein microspheres in which a gas such as perfluoropropane, perfluorobutane or perfluoropentane is contained.

9 Claims, No Drawings

U.S. PATENT DOCUMENTS

| | | |
|---|---|---|
| 4,957,656 A | 9/1990 | Cerny et al. |
| 4,985,550 A | 1/1991 | Charpiot et al. |
| 4,987,154 A | 1/1991 | Long |
| 4,993,415 A | 2/1991 | Long |
| 5,078,146 A | 1/1992 | Sato |
| 5,080,885 A | 1/1992 | Long, Jr. |
| 5,088,499 A | 2/1992 | Unger |
| 5,107,842 A | 4/1992 | Levene et al. |
| 5,114,703 A | 5/1992 | Wolf et al. |
| 5,123,414 A | 6/1992 | Unger |
| 5,137,928 A | 8/1992 | Erbel et al. |
| 5,141,738 A | 8/1992 | Rasor et al. |
| 5,147,631 A | 9/1992 | Glajch et al. |
| 5,149,319 A | 9/1992 | Unger |
| 5,155,215 A | 10/1992 | Ranney |
| 5,171,755 A | 12/1992 | Kakufman et al. |
| 5,205,290 A | 4/1993 | Unger |
| 5,209,720 A | 5/1993 | Unger |
| 5,230,882 A | 7/1993 | Unger |
| 5,260,496 A | 11/1993 | Meinert et al. |
| 5,271,928 A | 12/1993 | Schneider et al. |
| 5,281,408 A | 1/1994 | Unger |
| 5,284,645 A | 2/1994 | Long |
| 5,344,393 A | 9/1994 | Roth et al. |
| 5,350,571 A | 9/1994 | Kaufman et al. |
| 5,354,549 A | 10/1994 | Klaveness et al. |
| 5,406,950 A | 4/1995 | Brandenburger et al. |
| 5,413,774 A | 5/1995 | Schneider et al. |
| 5,425,366 A | 6/1995 | Reinhardt et al. |
| 5,445,813 A | 8/1995 | Schneider et al. |
| 5,487,390 A | 1/1996 | Cohen et al. |
| 5,501,863 A | 3/1996 | Rossling et al. |
| 5,508,021 A | 4/1996 | Grinstaff et al. |
| 5,512,268 A | 4/1996 | Grinstaff et al. |
| 5,529,766 A | 6/1996 | Klaveness et al. |
| 5,531,980 A * | 7/1996 | Schneider et al. .......... 424/9.52 |
| 5,536,489 A | 7/1996 | Lohrmann et al. |
| 5,547,656 A | 8/1996 | Unger |
| 5,552,133 A | 9/1996 | Lambert et al. |
| 5,556,610 A | 9/1996 | Yan et al. |
| 5,558,856 A | 9/1996 | Klaveness et al. |
| 5,558,857 A | 9/1996 | Klaveness et al. |
| 5,560,364 A | 10/1996 | Porter |
| 5,562,893 A | 10/1996 | Lohrmann |
| 5,567,413 A | 10/1996 | Klaveness et al. |
| 5,567,414 A | 10/1996 | Schneider et al. |
| 5,567,415 A | 10/1996 | Porter |
| 5,571,497 A | 11/1996 | Unger |
| 5,578,291 A | 11/1996 | Porter |
| 5,578,292 A | 11/1996 | Schneider et al. |
| 5,597,549 A | 1/1997 | Schneider et al. |
| 5,599,523 A | 2/1997 | Beller et al. |
| 5,605,673 A | 2/1997 | Schutt et al. |
| 5,606,973 A | 3/1997 | Lambert et al. |
| 5,611,344 A | 3/1997 | Bernstein et al. |
| 5,614,169 A | 3/1997 | Klaveness et al. |
| 5,618,514 A | 4/1997 | Schroder et al. |
| 5,626,833 A | 5/1997 | Schutt et al. |
| 5,637,289 A | 6/1997 | Klaveness et al. |
| 5,639,443 A | 6/1997 | Schutt et al. |
| 5,643,553 A | 7/1997 | Schneider et al. |
| 5,658,551 A | 8/1997 | Schneider et al. |
| 5,711,933 A | 1/1998 | Bichon et al. |

FOREIGN PATENT DOCUMENTS

| | | | |
|---|---|---|---|
| GB | 1044680 | 12/1963 | |
| JP | 2196730 | 10/1982 | |
| JP | 59067229 | 4/1984 | |
| JP | 63-60943 | 3/1988 | |
| JP | 57-177790 | 8/1990 | |
| SU | 1641280 A1 | 4/1991 | |
| SU | 1718798 A1 | 3/1992 | |
| WO | WO 80/02365 | 11/1980 | |
| WO | WO 89/06978 | 8/1989 | |
| WO | WO 90/01952 | 8/1989 | |
| WO | WO 89/10118 | 11/1989 | |
| WO | WO 90/07491 | 7/1990 | |
| WO | WO 91/09629 | 7/1991 | |
| WO | WO 91/12823 | 9/1991 | |
| WO | WO 91/15244 | 10/1991 | |
| WO | WO 91/18612 | 12/1991 | |
| WO | WO 92/02560 | 2/1992 | |
| WO | WO 92/05806 | 4/1992 | |
| WO | WO 92/08496 | 5/1992 | |
| WO | WO 92/15284 | 9/1992 | |
| WO | WO 92/17212 | 10/1992 | |
| WO | WO 92/17213 | 10/1992 | |
| WO | WO 92/18165 | 10/1992 | |
| WO | WO 92/18169 | 10/1992 | |
| WO | WO 92/21382 | 12/1992 | |
| WO | WO 92/22247 | 12/1992 | |
| WO | WO 93/00930 | 1/1993 | |
| WO | WO 93/00933 | 1/1993 | |
| WO | WO 93/01798 | 2/1993 | |
| WO | WO 93/05819 | 4/1993 | |
| WO | WO 93/06869 | 4/1993 | |
| WO | WO 93/07905 | 4/1993 | |
| WO | WO 93/10440 | 5/1993 | |
| WO | WO 93/17718 | 9/1993 | |
| WO | WO 94/06477 | 3/1994 | .......... A61K/49/00 |
| WO | WO 94/09829 | 5/1994 | |
| WO | WO 94/19101 | 9/1994 | |
| WO | WO 94/21301 | 9/1994 | |
| WO | WO 94/21302 | 9/1994 | |
| WO | WO 94/21303 | 9/1994 | |
| WO | WO 94/28939 | 12/1994 | |
| WO | WO 95/01187 | 1/1995 | |
| WO | WO 95/16467 | 6/1995 | .......... A61K/49/00 |
| WO | WO 97/29783 | 8/1997 | .......... A61K/49/00 |

OTHER PUBLICATIONS

Feinsten, Steven B., et al., Safety and Efficacy of a New Transpulmonary Ultrasound Contrast Agent: Initial Multicenter Clinical Results, Journal of American College of Cardiology, 16:316–24, Aug. 1990.

Feinsten, Steven B., et al., Microcardial Contrast Echocardiography: Examination of Infracoronary Injections. Microbubble Diameters and Video Intentisty Decay, American Journal of Physiologic Imaging 1:12–18 (1986).

Fobbe, V.F., et al., Farbkodierte Duplexsonographie Un Ultraschallkontrastmittel–Nachweis Von Renalen Perfusion-Defekten Im Tierexperiment, Fortschr. Röntgenstr. 154:242–245 (1991).

Handa, T., et al., Phospholipid Monolayers at the Triolein–Saline Interface: Production of Microemulsion Particles and Conversion of Monolayers to Bilayers, Biochemistry 29:2884–2890 (1990).

Kabalnov, A.S., et al., Safety and Efficacy of A New Transpulmonary Ultrasound Contrast Agent: Initial Multicenter Clinical Results. Journal of Fluorine Chemistry 50:271–284 (1990).

Keller, M.W., et al., Successful Left Ventricular Opacification Following Peripheral Venou Injection of Sonicated Contrast Agent: An Experimental Evaluation, American Heart Journal :570–575, Sep. 1987.

Long, David M., et al., Experiments with Radiopaque Perfluorocarbon Emulsions for Selective Opacification of Organs and Total Body Angiography, Investigative Radiology 15:242–247 (1980).

Marshall, Nissim, Encyclodedie Des Gas, Encyclopedia of Gas (1976).

Mattrey, Robert F., et al., Perfuorctylbromide: A Liver/Spleen–Specific and Tumor–Imaging Ultrasound Contrast Material, Radiology 145:759–752, Dec. 1982.

Meltzer, Richard S., et al., Transmission of Ultrasonic Contrast Through the Lungs, Ultrasound in Medicine and Biology, vol. 7, No. 4, pp. 377–384, 1981, Printed in Great Britain.

Meltzer, et al., Why do the Lungs Clear Ultrasonic Contrast?, Ultrasound in Medicine & Biology, 6:263–269 (1980).

Ohta, T., et al., Effect of the Contrast Agent and the Agitation Method on the Size, Number and Stability of Microbubbles: A Basic Experiment for the Myocardial Contrast Study, Japanese Journal of Medical Ultrasonics 18:318–325. (1991).

Ophir, J., et al., Contrast Agents in Diagnostic Ultrasound, Ultrasound in Medicine and Biology 15:319–333 (1989).

Schlief, R., Ultrasound Contrast Agents, Current Opinion in Radiology 3:198–207 (1991).

Schubert, K.V., et al., Microemulsifying Fluorinated Oils with Mixtures of Fluorinated and Hydrogenated Surfactants, Colloids and Surfaces: Physicochemical and Engineering Aspects 84:97–106 (1994).

Swanson, Dennis P., et al.; Pharmaceuticals in Medical Imaging, Radiopaque Contrast Media, Radiopharmaceuticals, Enhancement Agents for Magnetic Resonance Imaging and Ultrasound; Macmillan Pulishing Co., Chapter 22, pp. 682–685, (1990).

Szönyi, F., et al., Syntheses De Tensioactifs F–Alkyles Non Ioniques Monodisperses, Journal of Fluorine Chemistry 36:195–209 (1987).

Verescon, Christian, et al., An Easy, Convenient Was of Describing the Stability of Fluorocarbon Emulsions, Journal de Chimie Physique 86:2111–2116 (1989).

Violante, M.R., et al., Particle Stabilized Bubbles for enhanced Organ Ultrasound Imaging, Investigative Radiology 26:194–200, Nov. 1991.

Widder, Donald J., et al., Microbubbles as a Contrast Agent for Neurosonography and Ultrasound–Guided Catheter Manipulation: In Vitro Studies, AJR 147:347–352, Aug. 1986.

Zarif, Leila, et al., Synergistic Stabilization of Perfluorocarbon–Pluronic F–68 Emulsion by Perfluoroalkylated Polyhydroxylated Surgactants, Jaocks 66:10, Oct. 1989.

Ziskin, Marvin, C., et al., Contrast Agents for Diagnostic Ultrasound, Investigative Radiology 6:500–505 (1972).

Hilpert, P., *Contrast Agents in Diagnostic Ultrasound:* Mosby Year Book, Ch. 3, pps. 30–42 (1991).

Lincoff, A. et al.; *Intravitreal Expansion of Perfluorocarbon Bubbles;* Ophthalmology, vol. 98 (1980).

Lincoff, H., et al.; *Intravitreal Longevity of Three Perfluorocarbon Bubbles;* Arch. Ophthalmology, vol. 98, pps. 1610–1611 (1980).

Sakata, M., et al; *Acute Toxicity of Fluorocarbon–22: Toxic Symptons, Lethal Concentration, and its Fate in Rabbit and Mouse,* Toxicology and Applied Pharmacology 59, pp. 64–70 (1981).

Simaan, J. et al; *Hemodynamic Effects of a Aerosol Propellants I. Cardiac Depression in the Dog;* Toxicology, vol. 5, pp. 127–138 (1975).

Vygantas, C. et al.; *Octafluorocyclobutane and Other Gases for Vitreous Replacement;* Ophthalmology, vol. 90, (1993).

The Merck Index, pp. 1870 and 9772 (1996).

Dupont Technical Bulletin, pp.: 1–11 *"Freon: Technical Bulletin"* in Dupont Technical Bulletin, (E.I. Dupont De Nemours and Company, Wilmington, Delaware, 1964).

Dupont, pp. 1–10 *"'Freon' Fluorocarbons: Properties and Applications"* in Dupont Technical Bulletin, (E.I Dupont De Nemours and Company, Wilmington, Delaware, 1987).

Barnhart, J. et al.; *Air–Filled Albumin Microspheres for Echocardiography Contrast Enhancement,* Investigative Radiology Suppl. 1 vol. 25 (1990).

Feinsten, Steven; *Myocardial Perfusion Imaging: Contrast Echocardiography Today and Tomorrow,* JACC, vol. 8, No. 1 pp. 251–253, (1986).

Gardner, T. et al.; *A Survey of Intraocular Gas Use in North America,* Arch Ophthalmol. vol. 106, pp. 1188–1189 (1988).

Keller, M. et al.; *The Behavior of Sonicated Albumin Microbubbles Within the Microcirculation: a Basis for Their Use During Mycardial Contrast Echocardiography,* Circulation Research, vol. 65, No. 2, (1989).

Levene, H. et al.; *Characterization of Albunex,* J.Assoc. Soc. Am. Surp. 1, vol. 97 (1990).

Lincoff, A. et al.; *Perfluoro–n–Butane,* Arch Ophthalmol. vol. 101,pp. 460–462, (1983).

Rosecan, L. et al; *Therapeutic Ultrasound in the Treatment of Retinal Detachment: Clinical Observations and Light and Electron Microscopy,* Retina vol. 5, No. 2, (1985).

* cited by examiner

ULTRASOUND CONTRAST AGENTS INCLUDING PROTEIN STABILIZED MICROSPHERES OF PERFLUOROPROPANE, PERFLUOROBUTANE OR PERFLUOROPENTANE

RELATED APPLICATIONS

This is a continuation of prior application Ser. No. 08/380,085 filed on Jan. 30, 1995, now U.S. Pat. No. 5,558,854 for PERSISTENT GASEOUS BUBBLES AS ULTRASOUND CONTRAST MEDIA which is a Divisional Application of Ser. No. 07/936,011 filed on Sep. 2, 1992, abandoned, which is a Continuation-in-part Application of Ser. No. 07/893,657 filed on Jun. 5, 1992, now U.S. Pat. No. 5,409,688, which is a Continuation-in-part Application of Ser. No. 07/761,311 filed on Sep. 17, 1991, abandoned, of STEVEN C. QUAY.

DESCRIPTION

This invention relates to agents that enhance the contrast in an ultrasound image generated for use in medical diagnosis. The contrast-enhancing media disclosed herein are comprised of extremely small gas bubbles which are present in a solution that is infused into the body during or just before an ultrasound image is generated. This invention is also directed to a method for enhancing such images by selecting gases from which a collection of free gas microbubbles can be prepared that have novel and superior properties. These microbubbles, composed of the gases whose selection is enabled by the process of this invention, may be extremely small in size and yet survive in the bloodstream long enough to allow contrast-enhanced imaging of parts of the cardiovascular system, peripheral vascular system, and vital organs previously believed to be inaccessible to free gas microbubbles.

BACKGROUND

When using ultrasound to obtain an image of the internal organs and structures of a human or animal, ultrasound waves—waves of sound energy at a frequency above that discernable by the human ear—are reflected as they pass through the body. Different types of body tissue reflect the ultrasound waves differently and the reflections, often aptly described as "echoes," that are produced by the ultrasound waves reflecting off different internal structures are detected and converted electronically into a visual display. This display may prove invaluable to a physician or other diagnostician in several ways, including evaluating the progression of cardiovascular disease or the existence or nature of a tumor.

For some medical conditions, obtaining a useful image of the organ or structure of interest is especially difficult because the details of the structure may not be adequately discernible from the surrounding tissue in an ultrasound image produced by the reflection of ultrasound waves absent a contrast-enhancing agent. Additionally, traditional ultrasound images are notoriously poor in quality and resolution. For these reasons, detection and observation of certain physiological conditions may be substantially improved by enhancing the contrast in an ultrasound image by infusing an agent into an organ or other structure of interest. In other cases, detection of the movement of the contrast-enhancing agent itself is particularly important. For example, a distinct blood flow pattern that is known to result from particular cardiovascular abnormalities may only be discernible by infusing a contrasting agent into the bloodstream and observing the dynamics of the blood flow.

Medical researchers have made extensive investigation into the use of solids, gases and liquids in an attempt to discover ultrasound contrast-enhancing agents suitable for particular diagnostic purposes. Composite substances such as gelatin encapsulated microbubbles, gas-incorporated liposomes, sonicated partially denatured proteins and emulsions containing highly fluorinated organic compounds have also been studied in an attempt to develop an agent that has certain ideal qualities, primarily, stability in the body and the ability to provide significantly enhanced contrast in an ultrasound image.

Small bubbles of a gas, termed "microbubbles," are readily detected in an image produced using standard ultrasound imaging techniques. When infused into the bloodstream or a particular site in the body, microbubbles enhance the contrast between the region containing the microbubbles and the surrounding tissue.

A substantial amount of the research effort directed at contrast-enhancing agents has focused on the use of extremely small gas bubbles. Investigators have long known that free gas bubbles provide a highly effective contrast agent because a gas bubble has unique physical characteristics that affect ultrasound energy as it is directed through the body. The advantages offered by free gas bubbles as opposed to liquid or solid agents that exhibit contrast enhancement is described in detail below in the context of the discussion of ultrasound diagnostic techniques.

Despite the known advantages, however, the rapid dissolution of free gas bubbles in solutions such as blood or many aqueous intravenous solutions, severely limits their use as an ultrasound contrast-enhancing agent. The most important limitations are the size of the microbubble and the length of time that a microbubble will exist before dissolving into the solution.

Examining the size requirements for microbubbles more closely, the gas bubbles must, of course, be sufficiently small that a suspension of the bubbles does not carry the risk of embolism to the organism in which they are infused. At the same time, extremely small free gas bubbles composed of the gases generally used in ultrasound contrast imaging dissolve into solution so rapidly that their image-enhancing capability exists only immediately proximate to the infusion site. An additional obstacle exists for ultrasound imaging of the cardiovascular system. Medical researchers have studied the time required for microbubbles composed of ordinary air, pure nitrogen, pure oxygen, or carbon dioxide, to dissolve into solution. Microbubbles of these gases that are sufficiently small to be able to pass through the lungs and reach the left heart, less than about 8 microns in diameter, have a life span of less than approximately 0.25 seconds. Meltzer, R. S., Tickner, E. G., Popp, R. L., "Why Do the Lungs Clear Ultrasonic Contrast?" *Ultrasound in Medicine and Biology*, Vol. 6, p.263, 267 (1980). Since it takes over 2 seconds for blood to pass through the lungs, microbubbles of these gases would be fully dissolved during passage through the lungs and would never reach the left heart. Ibid. Primarily because of this tradeoff between bubble size and life span, many researchers concluded that free gas microbubbles were not useful as a contrast-enhancing agent for ultrasound diagnosis of certain parts of the cardiovascular system.

However, the ultrasound contrast-enhancing media described herein comprises microbubbles, composed of the biocompatible gases whose selection is also provided by this invention, that are sufficiently small that they pass through the pulmonary capillary diameter of approximately 8 microns and thereby allow contrast-enhanced ultrasound diagnosis of the left chambers of the heart. The free gas microbubbles survive in the bloodstream long enough that they may be peripherally intravenously infused, travel through the right heart, through the lungs, and into the left cardiac chambers without dissolving into solution. Additionally, certain of these media have extremely long persistence in solution and will enable contrast-enhancement of many other organs and structures.

This invention overcomes many of the inherent limitations thought to exist with the use of free gas microbubbles by providing, in part, a method for selecting special gases based on particular physical criteria such that microbubbles composed of these gases do not suffer from the same limitations as the microbubbles previously investigated. Therefore, it has been discovered that the ultrasound contrast-enhancing media described herein comprising a composition of microbubbles produced using a biocompatible gas or combination of gases selected by the physical and chemical parameters disclosed herein can exist for a sufficient length of time and be of sufficiently small size that their stability in the bloodstream allows enhanced ultrasound contrast imaging of particular structures in the body previously thought inaccessible to free gas microbubbles.

By using the term "biocompatible gas" I mean a chemical entity which is capable of performing its functions within or upon a living organism in an acceptable manner, without undue toxicity or physiological or pharmacological effects, and which is, at the temperature of the living organism, in a state of matter distinguished from the solid or liquid states by very low density and viscosity, relatively great expansion and contraction with changes in pressure and temperature, and the spontaneous tendency to become distributed uniformly throughout any container. The following Table contains the assumed body temperatures for various living organisms:

| Organism | Rectal Temperature (degree Fahrenheit) |
| --- | --- |
| Swine (*Sus Scrofa*) | 101.5–102.5 |
| Sheep (Ovis sp.) | 101–103 |
| Rabbit (*Oryctolaqus cuniculus*) | 102–103.5 |
| Rat (*Tattus morvegicus*) | 99.5–100.6 |
| Monkey (*Macaca mulatta*) | 101–102 |
| Mouse (*Mus Musculus*) | 98–101 |
| Goat (*Capra hircus*) | 101–103 |
| Guinea pig (*Cavia porcellus*) | 102–104 |
| Hamster (Mesocricetus sp.) | 101–103 |
| Ham (*Homo sapiens*) | 98.6–100.4 |
| Horse (Equus sp.) | 101–102.5 |
| Dog (*Canin familiaris*) | 101–102 |
| Baboon (Papio) | 98–100 |
| Cat (*Felis catus*) | 101–102 |
| Cattle (*Bos taurus*) | 101.5–102.5 |
| Chimpanzee (Pan) | 96–100 |

Techniques for Measuring Ultrasound Contrast-enhancement Phenomena

To more fully appreciate the subject matter of the present invention, it is useful to describe what is presently known about the technology of ultrasound imaging and to review the search for improved ultrasound contrast-enhancing agents in that light.

Materials that are useful as ultrasound contrast agents operate by having an effect on ultrasound waves as they pass through the body and are reflected to create the image from which a medical diagnosis is made. In an attempt to develop an efficient image-contrast agent, one skilled in the art recognizes that different types of substances affect ultrasound waves in different ways and to varying degrees. Moreover, certain of the effects caused by contrast-enhancing agents are more readily measured and observed than others. Thus, in selecting an ideal composition for a contrast-enhancing agent, one would prefer the substance that has the most dramatic effect on the ultrasound wave as it passes through the body. Also, the effect on the ultrasound wave should be easily measured. There are three main contrast-enhancing effects which can be seen in an ultrasound image: backscatter, beam attenuation, and speed of sound differential. Each of these effects will be described in turn.

A. Backscatter

When an ultrasound wave that is passing through the body encounters a structure, such as an organ or other body tissue, the structure reflects a portion of the ultrasound wave. Different structures within the body reflect ultrasound energy in different ways and in varying strengths. This reflected energy is detected and used to generate an image of the structures through which the ultrasound wave has passed. The term "backscatter" refers to the phenomena in which ultrasound energy is scattered back towards the source by a substance with certain physical properties.

It has long been recognized that the contrast observed in an ultrasound image may be enhanced by the presence of substances known to cause a large amount of backscatter. When such a substance is administered to a distinct part of the body, the contrast between the ultrasound image of this part of the body and the surrounding tissues not containing the substance is enhanced. It is well understood that, due to their physical properties, different substances cause backscatter in varying degrees. Accordingly, the search for contrast-enhancing agents has focused on substances that are stable and non-toxic and that exhibit the maximum amount of backscatter.

Making certain assumptions about the way a substance reflects ultrasound energy, mathematical formulae have been developed that describe the backscatter phenomenon. Working with these formulae, a skilled researcher can estimate the ability of gas, liquid, and solid contrast-enhancing agents to cause backscatter and the degree to which a particular substance causes measurable backscatter can be compared with other substances based on the physical characteristics known to cause the backscatter phenomenon. As a simple example, the ability of substance A to cause backscatter will be greater than substance B, if, all other factors being equal, substance A is larger than substance B. Thus, when both substances are encountered by an ultrasound wave, the larger substance scatters a greater amount of the ultrasound wave.

The capability of a substance to cause backscatter of ultrasound energy also depends on other characteristics of the substance such as its ability to be compressed. Of particular importance is the dramatic increase in backscatter caused by gas bubbles due to the bubble resonance phenomenon which is described below. When examining different substances, it is useful to compare one particular measure of the ability of a substance to cause backscatter known as the "scattering cross-section."

The scattering cross-section of a particular substance is proportional to the radius of the scatterer, and also depends on the wavelength of the ultrasound energy and on other physical properties of the substance, J. Ophir and K. J. Parker, *Contrast Agents in Diagnostic Ultrasound*, Ultrasound in Medicine & Biology, vol. IS, n. 4, p. 319, 323 (1989).

The scattering cross-section of a small scatterer, a, can be determined by a known equation:

$$\sigma = \left[\frac{4}{9}\pi a^2 (ka)^4\right]\left[\left|\frac{\kappa_s - \kappa}{\kappa}\right|^2 + \frac{1}{3}\left|\frac{3(\rho_s - \rho)}{2\rho_s - \rho}\right|^2\right]$$

where $\kappa = 2\pi/\lambda$, where $\lambda$ is the wavelength; a=the radius of the scatterer; $\kappa_s$=adiabatic compressibility of the scatterer; $\kappa$=adiabatic compressibility of the medium in which the scatterer exists, $\rho_s$=density of the scatterers and $\rho$=the density of the medium in which the scatterer exists. P. M. Morse and K. U. Ingard, *Theoretical Acoustics*, p. 427, McGraw Hill, New York (1968).

In evaluating the utility of different substances as image contrasting agents, one can use this equation to determine which agents will have the higher scattering cross-section and, accordingly, which agents will provide the greatest contrast in an ultrasound image.

Referring to the above equation, the first bracketed quantity in the above equation can be assumed to be constant for the purpose of comparing solid, liquid and gaseous scatterers. It can be assumed that the compressibility or a solid particle is much less than that of the surrounding medium and that the density of the particle is much greater. Using this assumption, the scattering cross section of a solid particle contrast-enhancing agent has been estimated as 1.75. Ophir and Parker, supra, at 325.

For a pure liquid scatterer, the adiabatic compressibility and density of the scatterer $\kappa_s$ and the surrounding medium $\kappa$ are likely to be approximately equal which would, from the above equation, yield the result that liquids would have a scattering cross-section of zero. However, liquids may exhibit some backscatter if large volumes of a liquid agent are present presumably because the term a in the first bracketed quantity in the above equation may become sufficiently large. For example, if a liquid agent passes from a very small vessel to a very large one such that the liquid occupies substantially all of the vessel the liquid may exhibit measurable backscatter. Nevertheless, in light of the above equation and the following, it is appreciated by those skilled in the art that pure liquids are relatively inefficient scatterers compared to free gas microbubbles.

It is known that changes in the acoustic properties of a substance are pronounced at the interface between two phases, i.e., liquid/gas, because the reflection characteristics of an ultrasound wave change markedly at this interface. Additionally, the scatter cross-section of a gas is substantially different than a liquid or solid, in part, because a gas bubble can be compressed to a much greater degree than a liquid or solid. The physical characteristics of gas bubbles in solution are known and standard values for compressibility and density figures for ordinary air can be used in the above equation. Using these standard values, the result for the second bracketed term alone in the above equation is approximately $10^{14}$, Ophir and Parker supra, at 325, with the total scattering cross section varying as the radius a of the bubble varies. Moreover, free gas bubbles in a liquid exhibit oscillatory motion such that, at certain frequencies, gas bubbles will resonate at a frequency near that of the ultrasound waves commonly used in medical imaging. As a result, the scattering cross-section of a gas bubble can be over a thousand times larger than its physical size.

Therefore, it is recognized that gas micro-bubbles are superior scatterers of ultrasound energy and would be an ideal contrast-enhancing agent if the obstacle of their rapid dissolution into solution could be overcome.

B. Beam Attenuation

Another effect which can be observed from the presence of certain solid contrast-enhancing agents, is the attenuation of the ultrasound wave. Image contrast has been observed in conventional imaging due to localized attenuation differences between certain tissue types. K. J. Parker and R. C. Wang, "Measurement of Ultrasonic Attenuation Within Regions selected from B-Scan Images," *IEEE Trans. Biomed. Enar. BME* 30(8), p. 431–37 (1983); K. J. Parker, R. C. Wang, and R. M. Lerner, "Attenuation of Ultrasound Magnitude and Frequency Dependence for Tissue Characterization," *Radiology*, 153(3), p. 785–88 (1984). It has been hypothesized that measurements of the attenuation of a region of tissue taken before and after infusion of an agent may yield an enhanced image. However, techniques based on attenuation contrast as a means to measure the contrast enhancement of a liquid agent are not well-developed and, even if fully developed, may suffer from limitations as to the internal organs or structures with which this technique can be used. For example, it is unlikely that a loss of attenuation due to liquid contrast agents could be observed in the image of the cardiovascular system because of the high volume of liquid contrast agent that would need to be present in a given vessel before a substantial difference in attenuation could be measured.

Measurement of the attenuation contrast caused by microspheres of Albunex (Molecular Biosystems, San Diego, Calif.) in vitro has been accomplished and it has been suggested that in Vivo attenuation contrast measurement could be achieved. H. Bleeker, K. Shung, J. Burnhart, "On the Application of Ultrasonic Contrast Agents for Blood Flowometry and Assessment of Cardiac Perfusion," *J. Ultrasound Med.* 9:461–471 (1990). Albunex is a suspension of 2–4 micron encapsulated air-filled microspheres that have been observed to have acceptable stability in vivo and are sufficiently small in size that contrast enhancement can occur in the left atrium or ventricle. Also, attenuation contrast resulting from iodipamide ethyl ester (IDE) particles accumulated in the liver has been observed. Under such circumstances, the contrast enhancement is believed to result from attenuation of the ultrasound wave resulting from the presence of dense particles in a soft medium. The absorption of energy by the particles occurs by a mechanism referred to as "relative motion." The change in attenuation caused by relative motion can be shown to increase linearly with particle concentration and as the square of the density difference between the particles and the surrounding medium. K. J. Parker, et al., "A Particulate Contrast Agent with Potential for Ultrasound Imaging of Liver," *Ultrasound in Medicine & Biology*, Vol. 13, No. 9, p. 555, 561 (1987). Therefore, where substantial accumulation of solid particles occurs, attenuation contrast may be a viable mechanism for observing image contrast enhancement although the effect is of much smaller magnitude than the backscatter phenomenon and would appear to be of little use in cardiovascular diagnoses.

C. Speed of Sound Differential

An additional possible technique to enhance contrast in an ultrasound image has been proposed based on the fact that the speed of sound varies depending on the media through which it travels. Therefore, if a large enough volume of an agent, through which the speed of sound is different than the surrounding tissue, can be infused into a target area, the difference in the speed of sound through the target area may be measurable. Presently, this technique is only experimental.

Therefore, considering the three techniques described above for contrast enhancement in an ultrasound image, the marked increase in backscatter caused by free gas microbubbles is the most dramatic effect and contrast-enhancing agents that take advantage of this phenomenon would be the most desirable if the obstacle of their limited stability in solution could be overcome.

The Materials Presently Used as Contrast-enhancing Agents

In light of what is known about the various techniques described above, attempts to develop a contrast-enhancing agent whose presence generates substantial contrast in an ultrasound image, and whose survival in vivo is sufficiently long to allow contrast-enhanced imaging of the cardiovascular system, has led to the investigation of a broad variety of substances—gases, liquids, solids, and combinations of these—as potential contrast-enhancing agents.

A. Solid Particles

Typically, the solid substances that have been studied as potential contrast-enhancing agents are extremely small particles that are manufactured in uniform size. Large numbers of these particles can be infused and circulate freely in the bloodstream or they may be injected into a particular structure or region in the body.

IDE particles are solid particles that can be produced in large quantities with a relatively narrow size distribution of approximately 0.5–2.0 microns. Sterile saline injections of these particles may be injected and will tend to accumulate in the liver. Once a substantial accumulation occurs, contrast enhancement may be exhibited by either attenuation contrast or backscatter mechanisms. Although suspensions comprising these solid particles dispersed in a liquid may exhibit acceptable stability, the backscatter or attenuation effects are relatively minor compared to free gas bubbles and a substantial accumulation of the particles must occur before appreciable contrast is observed in an ultrasound image. Thus, use of these suspensions has been limited to certain cell types in which the particles have the tendency to coagulate because unless the suspension becomes highly concentrated in particular tissue, the contrast enhancement will be minor.

SHU-454 (Schering, A. G., West Berlin, Germany) is an experimental contrast-enhancing agent in powder form that, when mixed with a saccharide diluent, forms a suspension of crystals of various rhomboid and polyhedral shapes ranging in size from 5 to 10 microns. Although the precise mechanism by which these crystals enhance ultrasound contrast is not completely understood, it is suspected that the crystals may trap microbubbles in their structure or that the crystals themselves may backscatter ultrasound energy by an as-yet undetermined mechanism.

B. Liquids and Emulsions

In another attempt to achieve a satisfactory agent, emulsions are prepared by combining a chemical species compatible with body tissue and a species that provides high ultrasound contrast enhancement. European Patent Application 0231091 discloses emulsions of oil in water containing highly fluorinated organic compounds that have been studied in connection with their possible use as a blood substitute and are also capable of providing enhanced contrast in an ultrasound image.

Emulsions containing perfluorooctyl bromide (PFOB) have also been examined. Perfluorooctyl bromide emulsions are liquid compounds known to have the ability to transport oxygen. PFOB emulsions have exhibited a limited utility as ultrasound contrast agents because of a tendency to accumulate in certain types of cells. Although the mechanism is not completely understood, PFOB emulsions may provide ultrasound contrast because of their high density and relatively large compressibility constant.

U.S. Pat. No. 4,900,540 describes the use of phospholipid-based liposomes containing a gas or gas precursor as a contrast-enhancing agent. A liposome is a microscopic, spherical vesicle, containing a bilayer of phospholipids and other amphipathic molecules and an inner aqueous cavity, all of which is compatible with the cells of the body. In most applications, liposomes are used as a means to encapsulate biologically active materials. The above reference discloses the use of a gas or gas precursors incorporated into the liposome core to provide a longer life span for the gas when infused into the body. Production of stable liposomes is an expensive and time consuming process requiring specialized raw materials and equipment.

C. Microbubbles

As noted above, a critical parameter that must be satisfied by a microbubble used as a contrast-enhancing agent is size. Free gas microbubbles larger than approximately 8 microns may still be small enough to avoid impeding blood flow or occluding vascular beds. However, microbubbles larger than 8 microns are removed from the bloodstream when blood flows through the lungs. As noted above, medical researchers have reported in the medical literature that microbubbles small enough to pass through the lungs will dissolve so quickly that contrast enhancement of left heart images is not possible with a free gas microbubble. Meltzer, R. S., Tickner, E. G., Popp, R. L., "Why Do the Lungs Clear Ultrasonic Contrast?" *Ultrasound in Medicine and Biology*, vol. 6, p.263, 267 (1980).

However, cognizant of the advantages to be gained by use of microbubbles as contrast-enhancing agents by virtue of their large scattering cross-section, considerable attention has been focused on developing mixtures ;containing microbubbles that are rendered stable in solution. Enhancing the stability of gas microbubbles may be accomplished by a number of techniques.

Each of the following techniques essentially involves suspending a collection of microbubbles in a substrate in which a bubble of ordinary gas is more stable than in the bloodstream.

In one approach, microbubbles are created in viscous liquids that are injected or infused into the body while the ultrasound diagnosis is in progress. The theory behind the use of viscous fluids involves an attempt to reduce the rate at which the gas dissolves into the liquid and, in so doing, provide a more stable chemical environment for the bubbles so that their lifetime is extended.

Several variations on this general approach have been described. EPO Application No. 0324938 describes a viscous solution of a biocompatible material, such as a human protein, in which microbubbles are contained. By submitting a viscous protein solution to sonication, microbubbles are formed in the solution. Partial denaturation of the protein by chemical treatment or heat provides additional stability to microbubbles in the solution by decreasing the surface tension between bubble and solution.

Therefore, the above approaches may be classified as an attempt to enhance the stability of microbubbles by use of a stabilizing medium in which the microbubbles are contained. However, none of these approaches have addressed the primary physical and chemical properties of gases which have seriously limited the use of free gas microbubbles in ultrasound diagnosis, particularly with respect to the cardiovascular system. None of these approaches suggest that selection of the gases, by precise criteria, would yield the ability to produce stable microbubbles at a size that would allow transpulmonary contrast-enhanced ultrasound imaging.

The behavior of microbubbles in solution can be described mathematically based on certain parameters and characteristics of the gas of which the bubble is formed and the solution in which the bubble is present. Depending on the degree to which a solution is saturated with the gas of which the microbubbles are formed, the survival time of the microbubbles can be calculated. P. S. Epstein, M. S. Plesset, "On the Stability of Gas Bubbles in Liquid-Gas Solutions," *The Journal of Chemical Physics*, Vol. 18, n. 11, 1505 (1950). Based on calculations, it is apparent that as the size of the bubble decreases, the surface tension between bubble and surrounding solution increases. As the surface tension increases, the rate at which the bubble dissolves into the solution increases rapidly and, therefore, the size of the bubble decreases more and more rapidly. Thus, the rate at which the bubble shrinks increases as the size of the bubble decreases. The ultimate effect of this is that a population of small free gas microbubbles composed of ordinary air dissolves so rapidly that the contrast-enhancing effect is extremely short lived. Using known mathematical formula, one can calculate that a microbubble of air that is 8 microns in diameter, which is small enough to pass through the lungs, will dissolve in between 190 and 550 milliseconds depending on the degree of saturation of the surrounding solution. Based on these calculations, medical investigators studying the way in which the lungs remove ultrasound contrast agent have calculated the dissolution times of oxygen and nitrogen gas microbubbles in human and canine blood and have concluded that free gas microbubble contrast agents will not allow contrast-enhanced imaging of the left ventricle because of the extremely brief life of the microbubbles.

The physical properties of the systems that feature gas bubbles or gases dissolved in liquid solutions have been investigated in detail including the diffusion of air bubbles formed in the cavitating flow of a liquid and the scatter of light and sound in water by gas bubbles.

The stability of gas bubbles in liquid-gas solution has been investigated both theoretically, Epstein P. S. and Plesset M. S., On the Stability of Gas Bubbles in Liquid-Gas Solutions, J. Chem. Phys. 18:1505–1509 (1950) and experimentally, Yang W J, Dynamics of Gas Bubbles in Whole Blood and Plasma, J. Biomech 4:119–125 (1971); Yang W J, Echigo R., Wotton D R, and Hwang J B, Experimental Studies of the Dissolution of Gas Bubbles in Whole Blood and Plasma-I. Stationary Bubbles. J. Biomech 3:275–281 (1971); Yang W J, Echigo R., Wotton D R, Hwang J B, Experimental Studies of the Dissolution of Gas Bubbles in Whole Blood and Plasma-II. Moving Bubbles or Liquids. J. Biomech 4:283–288 (1971). The physical and chemical properties of the liquid and the gas determine the kinetic and thermodynamic behavior of the system. The chemical properties of the system which influence the stability of a bubble, and accordingly the life time, are the rate and extent of reactions which either consume, transform, or generate gas molecules.

For example, a well known reaction that is observed between a gas and a liquid takes place when carbon dioxide gas is present in water. As the gas dissolves into the aqueous solution, carbonic acid is created by hydration of the carbon dioxide gas. Because carbon dioxide gas is highly soluble in water, the gas diffuses rapidly into the solution and the bubble size diminishes rapidly. The presence of the carbonic acid in the solution alters the acid-base chemistry of the aqueous solution and, as the chemical properties of the solution are changed by dissolution of the gas the stability of the carbon dioxide gas bubbles changes as the solution becomes saturated. In this system, the rate of dissolution of a gas bubble depends in part on the concentration of carbon dioxide gas that is already dissolved in solution.

However, depending on the particular gas or liquid present in the system, the gas may be substantially insoluble in the liquid and dissolution of a gas bubble will be slower. In this situation, it has been discovered that it is possible to calculate bubble stability in a gas-liquid system by examining certain physical parameters of the gas.

BRIEF DESCRIPTION OF THE INVENTION

It has been discovered that it is possible to identify chemical systems where extremely small gas bubbles are not reactive in an aqueous solution. Relying on the method disclosed herein one skilled in the art may specially select particular gases based on their physical and chemical properties for use in ultrasound imaging. These gases can be used to produce the contrast-enhancing media that is also the subject matter of this invention. The microbubbles can be produced using certain existing techniques that use ordinary air, and can be infused as in a conventional ultrasound diagnosis.

The method that is the subject matter of this invention requires that calculations be made, consistent with the equations provided herein, based on the intrinsic physical properties of a gas and a liquid. Particularly, the density of a gas, the solubility of a gas in solution, and the diffusivity of a gas in solution, which in turn is dependent on the molar volume of the gas and the viscosity of the solution, are used in the equations disclosed below. Thus, by the method disclosed herein, the physical properties of a given gas-liquid system can be evaluated, the rate and extent of bubble collapse can be estimated, and gases that would constitute effective contrast-enhancing agents can be selected based on these calculations. Using existing techniques, substantially improved contrast-enhancing media may then be produced and used to improve the quality and usefulness of ultrasound imaging.

DETAILED DESCRIPTION OF THE INVENTION

To understand the method of this invention, it is useful to derive the mathematical relationships that describe the parameters of a gas-liquid system and the effect on bubble stability that occurs when a value for one or more of these parameters is altered. It is assumed that, at an initial time, $T_0$, a spherical gas bubble of gas X, with a radius of $R_0$, is placed in a solution in which the initial concentration of gas X dissolved in the solution is equal to zero. Over some period of time, the bubble of gas X will dissolve into the solvent at which time its radius R will equal zero. Assume further that the solution is at constant temperature and pressure and that the dissolved gas concentration for a solution saturated with the particular gas is designated $C_s$. Thus, at $T_o$, the concentration of the gas in the solution is zero, meaning that none of the gas has yet dissolved and all of the gas that is present is still contained within the bubble of radius $R_0$.

As time progresses, due to the difference in the concentration of the gas in the bubble and the gas in solution, the bubble will tend to shrink as gas in the bubble is dissolved into the liquid by the process of diffusion. The change in bubble radius from its original radius of $R_0$ to, after the passage of a particular amount of time, a smaller radius R is expressed by Equation (1), $$\frac{R}{R_0} = \left[1 - \left(\frac{2DC_s}{\rho R_0^2}\right)T\right]^{1/2}$$

where R is the bubble radius at time T, D is the coefficient of diffusivity of the particular gas in the liquid, and ρ is the density of the particular gas of which the bubble is composed.

It follows that the time T required for a bubble to dissolve completely may be determined from Equation (1) by setting $R/R_0=0$, and solving for T:

$$T = \frac{R_0^2 \rho}{2DC_s} \qquad \text{Equation (2)}$$

This result qualitatively indicates that bubble stability, and hence life span, is enhanced by increasing the initial bubble size $R_0$ or by selecting a gas of higher density ρ, lower solubility $C_s$ in the liquid phase, or a lower coefficient of diffusivity D.

The diffusivity D of a gas in a liquid is dependent on the molar volume of the gas (Vm), and the viscosity of the solution (η) as expressed by a known Equation;

$$D = 13.26 \times 10^{-5} \cdot \eta^{-1.14} \cdot V_m^{-0.589} \qquad \text{(Equation 3)}$$

By substituting the expression for D given in Equation (3) into Equation (2) it is revealed that bubble stability is enhanced by using gases of larger molar volume Vm, which tend to have a higher molecular weight, and liquids of higher viscosity.

By way of example, a comparison of the stability of air microbubbles and microbubbles composed of gases specially selected by the method disclosed herein may be made. Taking the value of D for air in water at 22° C. as $2\times10^{-5}$ cm²sec⁻¹ and the ratio $C_s/\rho=0.02$ (Epstein and Plesset, Ibid.), one obtains the following data for the time t for complete solution of air bubbles in water (unsaturated with air):

TABLE I

| INITIAL BUBBLE DIAMETER, microns | TIME, milliseconds |
|---|---|
| 12 | 450 |
| 10 | 313 |
| 8 | 200 |
| 6 | 113 |
| 5 | 78 |
| 4 | 50 |
| 3 | 28 |
| 2 | 13 |
| 1 | 3 |

If the blood transit time from the pulmonary capillaries to the left ventricle is two seconds or more (Hamilton, W. F. editor, Handbook of Physiology, Vol. 2, section 2, CIRCULATION. American Physiology Society, Washington, D.C., p. 709, (1963)), and recognizing that only microbubbles of approximately 8 microns or less will be small enough to pass through the lungs, it is clear that none of these bubbles have a life span in solution long enough to be useful contrast agents for ultrasound contrast-enhanced imaging of the left ventricle.

The method of the present invention allows identification of potentially useful gases by comparing the properties of any particular gas, denoted gas X in the following description, to air. Taking Equations (2) and (3) above, a coefficient Q may be formulated for a particular gas X that will describe the stability of microbubbles composed of gas X in a given liquid. The value of the Q coefficient determined by this method for a particular gas X also can be used to determine the utility of gas X as an ultrasound contrast-enhancing agent as compared to ordinary air.

From Equation (2) above, an equation that describes the time for complete dissolution of a bubble of gas X compared to the same size bubble of ordinary air under identical conditions of solution temperature and solution viscosity may be written based on the physical properties of gas X and air:

Equation (4)

$$T_x = T_{air}\left[\frac{\rho_x}{\rho_{air}}\right]\left[\frac{(C_s)_{air}}{(C_s)_x}\right]\left[\frac{D_{air}}{13.26 \times 10^{-5} \cdot \eta^{-1.14} \cdot (V_m)_x^{-.589}}\right]$$

or, if D is known for gas X,
Equation (5)

$$T_x = T_{air}\left[\frac{\rho_x}{\rho_{air}}\right]\left[\frac{(C_s)_{air}}{(C_s)_x}\right]\left[\frac{D_{air}}{D_x}\right]$$

To formulate this equation so that the value Q may be obtained to enable comparison of gas X with air, the above equation may be rewritten:

$$T_x = QT_{air} \qquad \text{Equation (6)}$$

where $$Q = \left[\frac{\rho_x}{\rho_{air}}\right]\left[\frac{(C_s)_{air}}{(C_s)_x}\right]\left[\frac{D_{air}}{D_x}\right]$$

Assuming for comparison, a solution of water at 22 degrees C., the density, diffusivity, and solubility of air in the solution are known quantities which may be substituted into the above equation yielding:

$$Q = 4.0 \times 10^{-7} \left[\frac{\rho_x}{(C_x)_x D_x}\right] \qquad \text{Equation (7)}$$

Substituting Equation (3) into the above for gases whose diffusivity $D_x$ is not readily known, and assuming that the viscosity term n below for water at 22 degrees C. is approximately equal to 1.0 cP, $$Q = 3.0 \times 10^{-3} \left[\frac{\rho_x}{(C_s)_x (V_m)_x^{-.589}}\right] \qquad \text{Equation (8)}$$

Thus, knowing the density, solubility and molar volume of a gas, this method allows the calculation of the value of the Q coefficient.

If Q is less than one, microbubbles of gas X will be less stable in a given solvent than microbubbles of air. If Q is greater than one, microbubbles formed of gas X are more stable than microbubbles of air and will survive in solution longer than air bubbles. All other properties being the same for a given microbubble size, the time for complete dissolution of a microbubble of gas X is equal to the time for complete dissolution of a microbubble of ordinary air multiplied by the Q coefficient. For example, if the Q coefficient for gas X is 10,000, a microbubble of gas X will survive 10,000 times as long in solution compared to a microbubble of air. A Q value can be determined for any gas in any solution assuming the quantities identified herein are known or can be estimated.

Different methods for determining or estimating values for the individual parameters of density, diffusivity, and solubility may be needed depending on the chemical structure of the gas. Values for these parameters may or may not be available from known scientific literature sources such as the Gas Encyclopedia or the tabulations published by the American Chemical Society. Values for the density of most gases are readily available from sources such as the *Handbook of Chemistry and Physics*, CRC Press, 72d Ed. (1991–92). Additionally, the solubility in water and molar volume of some gases has been measured with accuracy. In many cases however, calculations for the numerical values for molar volume and solubility may need to be calculated or estimated to provide the data used to determine the value of the Q coefficient for an individual gas, by the method described above. An example of the calculation of Q values for a preferred selection of gases illustrates how the method of this invention can be applied to individual gases.

Generally, many fluorine-containing gases exhibit extremely low solubility in water, and have relatively high molecular weights, high molar volumes, and high densities. To determine the Q value for several gases, the solubility, molar volume and density of the individual gases are determined and the values are substituted into Equations (7) or (8) above.

Determination of Gas Solubility for Fluorocarbons

This method for estimating the gas solubility of fluorocarbons uses extrapolation of the experimental data of Kabalnov A S, Makarov K N, and Scherbakova O V. "Solubility of Fluorocarbons in Water as a Key Parameter Determining Fluorocarbon Emulsion Stability," *J. Fluor. Chem.* 50, 271–284, (1990). The gas solubility of these fluorocarbons is determined relative to perfluoro-n-pentane which has a water solubility of $4.0 \times 10^{-6}$ moles per liter. For a homologous series of non-branched fluorocarbons, the gas solubility may be estimated by increasing or reducing this value by a factor of about 8.0 for each increase or reduction in the number of additional —$CF_2$— groups present in the molecule.

Determination of Molar Volume

The molar volume (Vm) is estimated from the data of Bondi A., "Van der Waals Volumes and Radii," *J. Phys. Chem.* 68, 441–451 (1964). The molar volume of a gas can be estimated by identifying the number and type of atoms that make up the molecule of gas in question. By determining the number and type of atoms present in the molecule and how the individual atoms are bound to each other, known values may be applied for the molecular volume of the individual atoms. By considering the contribution of each individual atom and its frequency of occurrence, one may calculate the total molar volume for a particular gas molecule. This calculation is best demonstrated with an example.

It is known that a carbon molecule in an alkane carbon-carbon bond has a molar volume of 3.3 cubic centimeters per mole, a carbon atom in an alkene carbon-carbon bond has a molar volume of 10.0 cubic centimeters per mole, and when multiple fluorine atoms are bound to an alkane carbon, a fluorine atom has a molar volume of 6.0 cubic centimeters per mole.

Examining octafluoropropane, this molecule contains three carbon atoms in alkane carbon-carbon bonds (3 atoms at 3.3 cubic centimeters per mole) and 6 fluorine atoms bound to alkane carbons (6 atoms at 6.0 cubic centimeters per mole) hence, octafluoro-propane has a molar density of 58 cubic centimeters per mole.

Once density, molar volume, and solubility are determined, the Q value is calculated using Equation 8 above.

The following Table lists the Q value for a number of gases based on the calculations detailed above.

TABLE II

| GAS | DENSITY kg/m3 | SOLUBILITY micromoles/liter | MOLAR VOLUME cm3/mole | Q |
|---|---|---|---|---|
| Argon | 1.78 | 1500 | 17.9 | 20 |
| n-Butane | 2.05 | 6696 | 116 | 5 |
| Carbon Dioxide | 1.98 | 33000 | 19.7 | 1 |
| Decafluorobutane | 11.21 | 32 | 73 | 13,154 |
| Dodecafluoro-pentane | 12.86 | 4 | 183 | 207,437 |
| Ethane | 1.05 | 2900 | 67 | 13 |
| Ethyl ether | 2.55 | 977,058 | 103 | 0.1 |
| Helium | 0.18 | 388 | 8 | 5 |
| Hexafluorobuta-1,3-diene | 9 (*) | 2000 | 56 | 145 |
| Hexafluoro-2-butyne | 9 (*) | 2000 | 58 | 148 |
| Hexafluoroethane | 8.86 | 2100 | 43 | 116 |
| Hexafluoropropane | 10.3 | 260 | 58 | 1299 |
| Krypton | 3.8 | 2067 | 35 | 44 |
| Neon | 0.90 | 434 | 17 | 33 |
| Nitrogen | ## | ## | ## | 1 |
| Octafluoro-2-butene | 10 (*) | 220 | 65 | 1594 |
| Octafluorocyclo-butane | 9.97 | 220 | 61 | 1531 |
| Octafluoropropane | 10.3 | 260 | 58 | 1299 |
| Pentane | 2 | 1674 | 113 | 58 |
| Propane | 2.02 | 2902 | 90 | 30 |
| Sulfur Hexafluoride | 5.48 | 220 | 47 | 722 |
| Xenon | 5.90 | 3448 | 18 | 28 |

(*) These density values are estimated from the known density of homologous fluorocarbons.
The solubility/density ratio value of 0.02 (supra) and the diffusivity of $2 \times 10^{-5}$ cm$^2$sec-1 given above were used in equation 7 for this Q-value determination.

Once the Q value has been determined the utility of an individual gas as an ultrasound contrast-enhancing agent can be analyzed by determining the life span of a collection of microbubbles composed of the gas in question at different sizes, as was done for air in Table I above. Taking the value of Q for decafluorobutane and examining the time necessary for various sized bubbles to dissolve in water, one obtains the values in Table III below by multiplying each of the time values in Table I by the Q value for decafluorobutane:

TABLE III

| INITIAL BUBBLE DIAMETER, microns | TIME, minutes |
|---|---|
| 12 | 99 |
| 10 | 69 |
| 8 | 44 |
| 6 | 25 |
| 5 | 17 |
| 4 | 11 |
| 3 | 6.1 |
| 2 | 2.9 |
| 1 | 0.7 |

Notice that the time scale in Table III is minutes rather than milliseconds as was the case for air. All bubbles of decafluorobutane, even as small as 1 micron, can be injected peripherally and will not dissolve into solution during the approximately 10 seconds needed to reach the left ventricle.

Similar calculations can be performed for a gas with any Q coefficient. Slightly larger bubbles will be able to pass through the lungs and yet survive long enough to permit both examination of myocardial perfusion and dynamic abdominal organ imaging. Moreover, as with many of the gases identified by this method, decafluotobutane features low toxicity at small dosages and would, therefore, offer substantial advantages as a contrast-enhancing agent in conventional ultrasound diagnosis.

Manual creation of a microbubble suspension may be accomplished by several methods. U.S. Pat. No. 4,832,941, the disclosure of which is incorporated herein by reference, refers to a method for producing a suspension of microbubbles with a diameter less than seven microns created by spraying a liquid through a quantity of gas using a three-way tap. Although techniques could vary in practice, the three-way tap is a preferred method to manually suspend a quantity of high Q coefficient gas to produce the contrast-enhancing media described herein.

The general techniques for use of a three-way tap device are well known in connection with preparation of the common Freund's adjuvant for immunizing research animals. Typically, a three-way tap is comprised of a pair of syringes, both of which are connected to a chamber. The chamber has outlet from which the suspension may be collected or infused directly.

Techniques for use of the three-way tap may differ from that described in U.S. Pat. No. 4,832,941 because different gases are being used in this procedure. For example, use of one of the high Q coefficient gases disclosed herein may be more efficient if the system is purged of ordinary air or flushed with another gas before the microbubble suspension is produced.

In a preferred embodiment of the present invention, a 40–50% Sorbitol (D-glucitol) solution is mixed with approximately 1–10% by volume of a high Q-coefficient gas with approximately 5% gas being an optimal value. Sorbitol is a commercially available compound that when mixed in an aqueous solution substantially increases the viscosity of the solution. Higher viscosity solutions, as seen in equation 3 above, extend the life of a microbubble in solution. A 40–50% Sorbitol solution is preferred to maintain as a bolus upon injection; that is as intact as possible without exceeding a tolerable injection pressure. To produce the suspension of microbubbles, a quantity of the chosen gas is collected in a syringe. In the same syringe, a volume of the Sorbitol solution may be contained. A quantity of Sorbitol solution is drawn into the other syringe so that the sum of the two volumes yields the proper percentage of gas based on the volume percentage of microbubbles desired. Using the two syringes, each featuring a very small aperture, the liquid is sprayed into the gas atmosphere approximately 25 times or as many times as is necessary to create a suspension of microbubbles whose size distribution is acceptable for the purposes described herein. This technique may be varied slightly, of course, in any manner that achieves the resulting suspension of microbubbles of the desired size in a desired concentration. Microbubble size may be checked either visually or electronically using a Coulter Counter (Coulter Electronics) by a known method, Butler, B. D., "Production of Microbubble for Use as Echo Contrast Agents," *J. Clin. Ultrasound.* V.14 408 (1986).

EXAMPLES

Example 1

An ultrasound contrast agent was prepared using decafluorobutane as the microbubble-forming gas. A solution was prepared containing:

| | |
|---|---|
| sorbitol | 20.0 g |
| NaCl | 0.9 g |
| soy bean oil | 6.0 mL |
| Tween 20 | 0.5 mL |
| water q.s. | 100.0 mL |

A soapy, clear, yellow solution was afforded with stirring. A 10 mL aliquot of this solution was taken up in a 10 mL glass syringe. The syringe was then attached to a three-way stopcock. A second 10 mL syringe was attached to the stopcock and 1.0 cc of decafluorobutane (PCR, Inc., Gainesville, Fla.) was delivered to the empty syringe. The stopcock valve was opened to the solution-containing syringe and the liquid and gas phases mixed rapidly 20–30 times. A resulting milky-white, slightly viscous solution was obtained.

Example 2

The gas emulsion obtained in Example 1 was diluted with water (1:10 to 1:1000), placed in a hemocytometer, and examined under the microscope using an oil immersion lens. The emulsion consisted of predominately 2–5 micron bubbles. The density was 50–100 million microbubbles per mL of original undiluted formulation.

Example 3

The formulation of Example 1 was prepared and echocardiography performed in a canine model. A 17.5 kg mongrel dog was anesthetized with isoflurane and monitors established to measure ECG, blood pressure, heart rate, and arterial blood gases according to the methods described by Keller, M W, Feinstein, S B, Watson, D D: Successful left ventricular opacification following peripheral venous injection of sonicated contrast agent: An experimental evaluation. Am Heart J 114:570d (1987).

The results of the safety evaluation are as follows:

MAXIMUM PERCENTAGE CHANGE IN MEASURED PARAMETER WITHIN 5 MIN POST INJECTION

| DOSE | AORTIC PRESSURE | | | BLOOD GASES | | | HEART RATE |
|---|---|---|---|---|---|---|---|
| | SYSTOLIC | DIASTOLIC | | | | | |
| | mm Hg | | MEAN | PaO2 | PaCO2 | pH | |
| 0.5 mL | +6, −14 | +9, 0 | +8, −6 | 329 | 58.1 | 7.26 | +10 −19 |
| 1.0 mL | +9, −2 | +5, −1 | +4, −4 | | | | +1, −4 |

-continued

| | AORTIC PRESSURE | | | BLOOD GASES | | | |
|---|---|---|---|---|---|---|---|
| | SYSTOLIC | DIASTOLIC | | | | | |
| DOSE | mm Hg | | MEAN | PaO2 | PaCO2 | pH | HEART RATE |
| 2.0 mL | +5, −3 | +5, −1 | +5, −1 | | | | 0, −1 |
| 3.0 mL | +6, −2 | +7, 0 | +4, −3 | | | | 0, −3 |
| 4.0 mL | +5, −1 | +3, −3 | +5, −3 | | | | 0, −3 |
| 5.0 mL | 0, −10 | +1, −3 | 0, −4 | | | | +1, −1 |
| 7.0 mL | 0, −13 | 0, −8 | 0, −9 | 313 | 28.6 | 7.36 | 0, −1 |

All changes were transient and returned to baseline values typically within 3–6 minutes. The above safety data demonstrate minimal changes in the measured hemodynamic parameter. All doses provided both right and left ventricular chamber opacification. The intensity increased with the increasing dose.

EXAMPLE 4

The above specific determinations of the suitability of a particular gas for use as an ultrasound agent can be approximated if the molecular weight of a particular gas is known, can be calculated, or can be measured. This approximation is based on the determination that there is a linear relationship between the logarithm of the Q-value and the molecular weight for a gas.

Thus, the following guidelines can be used to estimate a Q-value:

| Molecular Weight | Estimated Q-value |
|---|---|
| <35 | <5 |
| 35–70 | 5–20 |
| 71–100 | 21–80 |
| 101–170 | 81–1000 |
| 171–220 | 1001–10,000 |
| 221–270 | 10,001–100,000 |
| >270 | >100,000 |

The following Table contains a series of gases with the relevant data on molecular weight and estimated Q-value. The higher the Q-value the more promising is the particular gas. Especially promising are gases with Q-values greater than five. Additional issues, including, but not limited to, cost and toxicity, should be considered in addition to longevity of the derived microbubbles (as estimated by the Q-value) in determining the suitability of any particular gas as an ultrasound contrast agent.

TABLE IV

| Chemical Name | Molecular Weight | Estimated Q Value |
|---|---|---|
| Acetone, hexafluoro | 166.02 | 81–1000 |
| Acetylene, isopropyl | 68 | 5–20 |
| Air | 28.4 | <5 |
| Allene | 40.06 | 5–20 |
| Allene, tetrafluoro | 112.03 | 81–1000 |
| Argon | 39.98 | 5–20 |
| Borne, dimethyl, methoxy | 71.19 | 21–80 |
| Borne, trimethyl | 55.91 | 5–20 |
| Boron fluoride dihydrate | 103.84 | 81–1000 |
| 1,2-Butadiene | 54.09 | 5–20 |
| 1,3-Butadiene | 54.09 | 5–20 |

TABLE IV-continued

| Chemical Name | Molecular Weight | Estimated Q Value |
|---|---|---|
| 1,3-Butadiene, 1,2,3-trichloro | 157.43 | 81–1000 |
| 1,3-Butadiene, 2-fluoro | 72.08 | 21–80 |
| 1,3-Butadiene, 2-methyl | 68.12 | 5–20 |
| 1,3-Butadiene, hexafluoro | 162.03 | 81–1000 |
| Butadiyne | 50.06 | 5–20 |
| n-Butane | 58.12 | 5–20 |
| Butane, 1-fluoro | 76.11 | 21–80 |
| Butane, 2-methyl | 72.15 | 21–80 |
| Butane, decafluoro | 238.03 | 10,001–100,000 |
| 1-Butene | 56.11 | 5–20 |
| 2-Butene {cis} | 56.11 | 5–20 |
| 2-Butene {trans} | 56.11 | 5–20 |
| 1-Butene, 2-methyl | 70.13 | 5–20 |
| 1-Butene, 3-methyl | 70.13 | 5–20 |
| 2-Butene, 3-methyl | 68 | 5–20 |
| 1-Butene, perfluoro | 200.03 | 1001–10,000 |
| 2-Butene, perfluoro | 200.03 | 1001–10,000 |
| 3-Butene-2-one, 4-phenyl {trans} | 146.19 | 81–1000 |
| 1-Butene-3-yne, 2-methyl | 66.1 | 5–20 |
| Butyl nitrite | 103.12 | 81–100 |
| 1-Butyne | 54.09 | 5–20 |
| 2-Butyne | 54.09 | 5–20 |
| Butyne, 2-chloro-1,1,1,4,4,4-hexafluoro | 199 | 1001–10,000 |
| 1-Butyne, 3-methyl | 68.12 | 5–20 |
| 2-Butyne, perfluoro | 162.03 | 81–1000 |
| Butyraldehyde, 2-bromo | 151 | 81–1000 |
| Carbon dioxide | 44.01 | 5–20 |
| Carbonyl sulfide | 60.08 | 5–20 |
| Crotononitrile | 67.09 | 5–20 |
| Cyclobutane | 56.11 | 5–20 |
| Cyclobutane, methyl | 70.13 | 5–20 |
| Cyclobutane, octafluoro | 200.03 | 1001–100,000 |
| Cyclobutene, perfluoro | 162.03 | 81–1000 |
| Cyclopentene, 3-chloro | 102.56 | 81–1000 |
| Cyclopropane | 42.08 | 5–20 |
| Cyclopropane, 1,2-dimethyl {trans, d1} | 70.13 | 5–20 |
| Cyclopropane, 1,1-dimethyl | 70.13 | 5–20 |
| Cyclopropane, 1,2-dimethyl {cis} | 70.13 | 5–20 |
| Cyclopropane, 1,2-dimethyl {trans, 1} | 70.13 | 5–20 |
| Cyclopropane, ethyl | 70.13 | 5–20 |
| Cyclopropane, methyl | 56.11 | 5–20 |
| Deuterium | 4.02 | <5 |
| Diacetylene | 50.08 | 5–20 |
| Diaziridine, 3-ethyl-3-methyl | 86.14 | 21–80 |
| Diazoethane, 1,1,1-trifluoro | 110.04 | 81–1000 |
| Dimethyl amine | 45.08 | 5–20 |
| Dimethyl amine, hexafluoro | 153.03 | 81–1000 |
| Dimethyl disulfide, hexafluoro | 202.13 | 1001–10,000 |
| Dimethylethylamine | 73.14 | 21–80 |
| bis-(Dimethyl phosphino) amine | 137.1 | 81–1000 |
| 2,3-Dimethyl-2-norbornano | 140.23 | 81–1000 |
| Dimethylamine, perfluoro | 171.02 | 1001–10,000 |
| Dimethyloxonium chloride | 82.53 | 21–80 |
| 1,3-Dioxolane-2-one, 4-methyl | 102.09 | 81–1000 |
| Ethane | 30.07 | <5 |
| Ethane, 1,1,1,2-tetrafluoro | 102.03 | 81–1000 |
| Ethane, 1,1,1-trifluoro | 84.04 | 21–80 |
| Ethane, 1,1,2,2-tetrafluoro | 102.03 | 81–1000 |

TABLE IV-continued

| Chemical Name | Molecular Weight | Estimated Q Value |
|---|---|---|
| Ethane, 1,1,2-trichloro-1,2,2-trifluoro | 187.38 | 1001–10,000 |
| Ethane, 1,1-dichloro | 98 | 21–80 |
| Ethane, 1,1-dichloro-1,2,2,2-tetrafluoro | 170.92 | 1001–10,000 |
| Ethane, 1,1-dichloro-1-fluoro | 116.95 | 81–1000 |
| Ethane, 1,1-difluoro | 66.05 | 5–20 |
| Ethane, 1,2-dichloro-1,1,2,2-tetrafluoro | 170.92 | 1001–10,000 |
| Ethane, 1,2-difluoro | 66.05 | 5–20 |
| Ethane, 1-chloro-1,1,2,2,2-pentafluoro | 154.47 | 81–1000 |
| Ethane, 1-chloro-1,1,2,2-tetrafluoro | 136.48 | 81–1000 |
| Ethane, 2-chloro,1,1-difluoro | 100 | 21–80 |
| Ethane, 2-chloro-1,1,1-trifluoro | 118.49 | 81–1000 |
| Ethane, Chloro | 64.51 | 5–20 |
| Ethane, chloro pentafluoro | 154.47 | 81–1000 |
| Ethane, dichlorotrifluoro | 152 | 81–1000 |
| Ethane, fluoro | 48.06 | 5–20 |
| Ethane, hexafluoro | 138.01 | 81–1000 |
| Ethane, nitro-pentafluoro | 165.02 | 81–1000 |
| Ethane, nitroso-pentafluoro | 149.02 | 81–1000 |
| Ethane, perfluoro | 138.01 | 81–1000 |
| Ethyl amine, perfluoro | 171.02 | 1001–100,000 |
| Ethyl ether | 74.12 | 21–80 |
| Ethyl methyl ether | 60.1 | 5–20 |
| Ethyl vinyl ether | 72.11 | 21–80 |
| Ethylene | 28.05 | <5 |
| Ethylene, 1,1-dichloro | 96.94 | 21–80 |
| Ethylene, 1,1-dichloro-2-fluoro | 114.93 | 81–1000 |
| Ethylene, 1,2-dichloro-1,2-difluoro | 132.92 | 81–1000 |
| Ethylene, 1,2-difluoro | 64 | 5–20 |
| Ethylene, 1-chloro-1,2,2-trifluoro | 116.47 | 81–1000 |
| Ethylene, chloro trifluoro | 116.47 | 81–1000 |
| Ethylene, dichloro difluoro | 132.92 | 81–1000 |
| Ethylene, tetrafluoro | 100.02 | 21–80 |
| Fulvene | 78.11 | 21–80 |
| Helium | 4 | <5 |
| 1,5-Heptadiyne | 92.14 | 21–80 |
| Hydrogen (H2) | 2.02 | <5 |
| Isobutane | 58.12 | 5–20 |
| Isobutane, 1,2-epoxy-3-chloro | 106.55 | 81–1000 |
| Isobutylene | 56.11 | 5–20 |
| Isoprene | 68.12 | 5–20 |
| Krypton | 83.8 | 21–80 |
| Methane | 16.04 | <5 |
| Methane sulfonyl chloride, trifluoro | 168.52 | 81–1000 |
| Methane sulfonyl fluoride, trifluoro | 152.06 | 81–1000 |
| Methane, (pentafluorothio)trifluoro | 196.06 | 1001–10,000 |
| Methane, bromo difluoro nitroso | 159.92 | 81–1000 |
| Methane, bromo fluoro | 112.93 | 81–1000 |
| Methane, bromo-chloro-fluoro | 147.37 | 81–1000 |
| Methane, bromo-trifluoro | 148.91 | 81–1000 |
| Methane, chloro difluoro nitro | 131.47 | 81–1000 |
| Methane, chloro dinitro | 140.48 | 81–1000 |
| Methane, chloro fluoro | 68.48 | 5–20 |
| Methane, chloro trifluoro | 104.46 | 81–1000 |
| Methane, chloro-difluoro | 86.47 | 21–80 |
| Methane, dibromo difluoro | 209.82 | 1001–10,000 |
| Methane, dichloro difluoro | 120.91 | 81–1000 |
| Methane, dichloro-fluoro | 102.92 | 81–1000 |
| Methane, difluoro | 52.02 | 5–20 |
| Methane, difluoro-iodo | 177.92 | 1001–10,000 |
| Methane, disilano | 76.25 | 21–80 |
| Methane, fluoro | 34.03 | <5 |
| Methane, iodo- | 141.94 | 81–1000 |
| Methane, iodo-trifluoro | 195.91 | 1001–10,000 |
| Methane, nitro-trifluoro | 115.01 | 81–1000 |
| Methane, nitroso-trifluoro | 99.01 | 21–80 |
| Methane, tetrafluoro | 88 | 21–80 |
| Methane, trichlorofluoro | 137.37 | 81–1000 |
| Methane, trifluoro | 70.01 | 5–20 |
| Methanesulfenylchloride, trifluoro | 136.52 | 81–1000 |
| 2-Methyl butane | 72.15 | 21–80 |
| Methyl ether | 46.07 | 5–20 |
| Methyl isopropyl ether | 74.12 | 21–80 |
| Methyl nitrite | 61.04 | 5–20 |
| Methyl sulfide | 62.13 | 5–20 |
| Methyl vinyl ether | 58.08 | 5–20 |
| Neon | 20.18 | <5 |
| Neopentane | 72.15 | 21–80 |
| Nitrogen (N2) | 28.01 | <5 |
| Nitrous oxide | 44.01 | 5–20 |
| 1,2,3-Nonadecane tricarboxylic acid, 2- . . . hydroxytrimethylester | 500.72 | >100,000 |
| 1-Nonene-3-yne | 122.21 | 81–1000 |
| Oxygen (O2) | 32 | <5 |
| 1,4-Pentadiene | 68.12 | 5–20 |
| n-Pentane | 72.15 | 21–80 |
| Pentane, perfluoro | 288.04 | >100,000 |
| 2-Pentanone, 4-amino-4-methyl | 115.18 | 81–1000 |
| 1-Pentene | 70.13 | 5–20 |
| 2-Pentene {cis} | 70.13 | 5–20 |
| 2-Pentene {trans} | 70.13 | 5–20 |
| 1-Pentene, 3-bromo | 149.03 | 81–1000 |
| 1-Pentene, perfluoro | 250.04 | 10,001–100,000 |
| Phthalic acid, tetrachloro | 303.91 | >100,000 |
| Piperidine, 2,3,6-trimethyl | 127.23 | 81–1000 |
| Propane | 44.1 | 5–20 |
| Propane, 1,1,1,2,2,3-hexafluoro | 152.04 | 81–1000 |
| Propane, 1,2-epoxy | 58.08 | 5–20 |
| Propane, 2,2-difluoro | 80.08 | 21–80 |
| Propane, 2-amino | 59.11 | 5–20 |
| Propane, 2-chloro | 78.54 | 21–80 |
| Propane, heptafluoro-1-nitro | 215.03 | 1001–10,000 |
| Propane, heptafluoro-1-nitroso | 199.03 | 1001–10,000 |
| Propane, perfluoro | 188.02 | 1001–10,000 |
| Propene | 42.08 | 5–20 |
| Propyl, 1,1,1,2,3,3-hexafluoro-2,3-dichloro | 221 | 10,001–100,000 |
| Propylene, 1-chloro | 76.53 | 21–80 |
| Propylene, 1-chloro-{trans} | 76.53 | 5–20 |
| Propylene, 2-chloro | 76.53 | 5–20 |
| Propylene, 3-fluoro | 60.07 | 5–20 |
| Propylene, perfluoro | 150.02 | 81–1000 |
| Propyne | 40.06 | 5–20 |
| Propyne, 3,3,3-trifluoro | 94.04 | 21–80 |
| Styrene, 3-fluoro | 122.14 | 81–1000 |
| Sulfur hexafluoride | 146.05 | 81–1000 |
| Sulfur (di),decafluoro(S2F10) | 298 | >100,000 |
| Toluene, 2,4-diamino | 122.17 | 81–1000 |
| Trifluoroacetonitrile | 95.02 | 21–80 |
| Trifluoromethyl peroxide | 170.01 | 81–1000 |
| Trifluoromethyl sulfide | 170.07 | 81–1000 |
| Tungsten hexafluoride | 298 | >100,000 |
| Vinyl acetylene | 52.08 | 5–20 |
| Vinyl ether | 70 | 5–20 |
| Xenon | 131.29 | 81–1000 |

Example 5

The relationship between a calculated Q-value for a given gas and the persistence of microbubbles of that gas was studied to determine what Q-value would be a lower limit for utility as an ultrasound contrast agent. For these experiments, a 190×100 mm Pyrex™ (No. 3140) evaporation dish was filled with approximately 2000 mL of water at 37° C. Five mL of a 20% sorbitol solution was taken up in a 10 mL syringe connected to a three way stopcock. A 10 mL syringe, containing 2 cubic centimeters of the subject gas (or low boiling liquid, as pertinent) was attached to the syringe containing the sorbitol solution. The sorbitol and gas or liquid are rapidly mixed 25-times to create a suspension of microbubbles or dispersed liquid and then rapidly added to the water. The microbubbles of this method are generally about 100 microns in size, and if composed of air would have a calculated persistence of 31 sec (0.5 min). Ultrasound scans before, during and after the addition were made with a Hewlett-Packard Model Sonos 500 ultrasound scanner operating at 5 MHz. The time during which the microbubbles could be observed was recorded. The results are contained in Table V below. The experimental Q-values were obtained by dividing the measured persistence of a given gas by the measured persistence for air.

TABLE V

RELATIONSHIP BETWEEN Q-VALUE FOR A GAS AND THE PERSISTENCE OF MICROBUBBLES

| GAS | Q-VALUE (Calculated) | PERSISTENCE (Experimental Q-Value) |
|---|---|---|
| Diethyl ether | 0.1 | 0.1 min (0.2) |
| Air | 1 | 0.6 min (1.0) |
| Butane | 5 | 1.5 min (2.6) |
| Helium | 5 | 2.0 min (3.5) |
| Propane | 30 | 3.2 min (6.0) |
| Pentane | 58 | 20.6 min (36) |
| Dodecafluoropentane | 207,437 | >5760 min (>10,105) |

These experiments indicate an excellent agreement between the calculated Q-value and the experimentally determined values. Based on these data, gases with Q-values calculated to be greater than five should be potentially useful as contrast agents for ultrasound imaging.

Example 6

The relationship of the state of matter of a given chemical entity with a high Q-coefficient and its utility as an ultrasound contrast agent was tested by comparing the efficiency of perfluoropentane and perfluorohexane to act as an ultrasound contrast agent. Perfluoropentane (dodecafluoropentane) has a calculated Q-coefficient of 207,437 and a boiling point under standard pressure conditions of 29.5 degrees Centigrade. Perfluorohexane (PCR, INc., Gainsville, Fla.) has a calculated Q-coefficient of 1,659,496 and a boiling point under standard pressure conditions of 59–60 degrees C. Therefore, at 37 degrees C., the body temperature of man, perfluoropentane is a gas while perfluorohexane is a liquid.

Aqueous dispersions of perfluoropentane and perfluorohexane (2% w/v) were formed at 4 degrees C. by vigorous homogenization. A plastic beaker, containing approximately 1000 mL of water at 37 degrees C., was prepared to simulate human blood and was ultrasonically-scanned, as indicated in Example 5 above, before and after the addition of samples of each of the above dispersions.

Less than 1.0 mL of the perfluoropentane dispersion, when mixed with the simulated blood, produced an extremely bright ultrasound signal which persisted for at least 30 minutes. A 1:10,000 dilution was still detectable.

In contrast, a 1.0 mL sample of the perfluorohexane dispersion was undetectable by ultrasound scanning under the same conditions, as was even a 10 mL sample (1:100 dilution).

The conclusion to be drawn is that both a high Q-coefficient and a gaseous state at the body temperature of the organism being scanned is necessary for a substance to be effective as an ultrasound contrast agent according to the method that is the subject matter of this invention.

Although the invention has been described in some respects with reference to specified preferred embodiments thereof, variations and modifications will become apparent to those skilled in the art. It is, therefore, the intention that the following claims not be given a restrictive interpretation but should be viewed to encompass variations and modifications that are derived from the inventive subject matter disclosed. In this regard the invention allows those skilled in the art to determine the suitability of various chemicals as ultrasound contrast agents where density, solubility and molar volume data are available.

I claim:

1. Biocompatible ultrasound contrast media comprising a solution in which microbubbles of a gas are stabilized by human protein, the gas comprising perfluoropropane.

2. Biocompatible ultrasound contrast media as in claim 1 wherein said human protein is denatured by heat or chemical treatment.

3. Biocompatible ultrasound contrast media as in claim 1 wherein said microbubbles are formed by sonication.

4. Biocompatible ultrasound contrast media comprising a solution in which microbubbles of a gas are stabilized by human protein, the gas comprising perfluorobutane.

5. Biocompatible ultrasound contrast media as in claim 4 wherein said human protein is denatured by heat or chemical treatment.

6. Biocompatible ultrasound contrast media as in claim 4 wherein said microbubbles are formed by sonication.

7. Biocompatible ultrasound contrast media comprising a solution in which microbubbles of a gas are stabilized by human protein, the gas comprising perfluoropentane.

8. Biocompatible ultrasound contrast media as in claim 7 wherein said human protein is denatured by heat or chemical treatment.

9. Biocompatible ultrasound contrast media as in claim 7 wherein said microbubbles are formed by sonication.

* * * * *

UNITED STATES PATENT AND TRADEMARK OFFICE
CERTIFICATE OF CORRECTION

PATENT NO.    : 6,723,303 B1
DATED         : April 20, 2004
INVENTOR(S)   : Steven C. Quay It is certified that error appears in the above-identified patent and that said Letters Patent is hereby corrected as shown below:

<u>Title page,</u>
Item [*] Notice, should read -- Subject to any disclaimer, the term of this patent is extended or adjusted under 35 U.S.C. 154(b) by 1,675 days. --.

Signed and Sealed this

Twenty-third Day of May, 2006

JON W. DUDAS
*Director of the United States Patent and Trademark Office*